(12) United States Patent
Guo

(10) Patent No.: US 11,786,465 B2
(45) Date of Patent: Oct. 17, 2023

(54) MICROEMULSION MIXTURE AND METHOD OF USING THE SAME, AND PHARMACEUTICAL MICROEMULSION MIXTURE AND METHOD OF USING THE SAME

(71) Applicant: CATHAY GENERAL HOSPITAL, Taipei (TW)

(72) Inventor: Jiun-Wen Guo, Taipei (TW)

(73) Assignee: CATHAY GENERAL HOSPITAL, Taipei (TW)

( * ) Notice: Subject to any disclaimer, the term of this patent is extended or adjusted under 35 U.S.C. 154(b) by 0 days.

(21) Appl. No.: 17/689,457

(22) Filed: Mar. 8, 2022

(65) Prior Publication Data
US 2022/0296513 A1    Sep. 22, 2022

(30) Foreign Application Priority Data

Mar. 19, 2021 (TW) .................................. 110109930

(51) Int. Cl.
| | |
|---|---|
| *A61K 9/107* | (2006.01) |
| *A61K 31/573* | (2006.01) |
| *A61K 47/10* | (2017.01) |
| *A61Q 19/00* | (2006.01) |
| *A61K 8/06* | (2006.01) |
| *A61K 8/63* | (2006.01) |
| *A61Q 17/00* | (2006.01) |
| *A61K 47/44* | (2017.01) |

(52) U.S. Cl.
CPC ............ *A61K 9/1075* (2013.01); *A61K 8/068* (2013.01); *A61K 8/63* (2013.01); *A61K 31/573* (2013.01); *A61K 47/10* (2013.01); *A61K 47/44* (2013.01); *A61Q 17/005* (2013.01); *A61Q 19/007* (2013.01)

(58) Field of Classification Search
CPC ........ A61K 9/1075; A61K 8/068; A61K 8/63; A61K 31/573; A61K 47/10; A61K 47/44; A61K 8/31; A61K 8/37; A61K 8/39; A61K 8/66; A61K 8/891; A61K 8/922; A61K 2800/782; A61K 9/0014; A61Q 17/005; A61Q 19/007; A61Q 19/00; A61P 17/06

See application file for complete search history.

(56) References Cited

U.S. PATENT DOCUMENTS 8,574,562 B2 * 11/2013 Goebel ................ A61K 9/1075
424/78.05

FOREIGN PATENT DOCUMENTS

| WO | WO-2016015094 A1 * | 2/2016 | ........... A61K 31/135 |
| WO | WO-2018148338 A1 * | 8/2018 | ............... A23L 5/00 |

OTHER PUBLICATIONS

Hwang. Enhanced Expression of Proliferating Cell Nuclear Antigen in Psoriatic Epidermis. Chonju Skin Clinic. 1994 (Year: 1994).*
Taiwan Patent Office, Office Action dated Jan. 26, 2022.
Jiun-Wen Guo et al., Salvianolic Acid B in Microemulsion Formulation Provided Sufficient Hydration for Dry Skin and Ameliorated the Severity of Imiquimod-induced Psoriasis-like Dermatitis in Mice, 2020.
Zichao Rao et al., Inhibitive Effect of Cremophor RH40 or Tween 80-based Self-microemulsiflying Drug Delivery System on Cytochrome P450 3A Enzymes in Murine Hepatocytes, 2010.

* cited by examiner

*Primary Examiner* — Robert A Wax
*Assistant Examiner* — John Seungjai Kwon
(74) *Attorney, Agent, or Firm* — WPAT, P.C

(57) ABSTRACT

The present invention provides a microemulsion mixture, comprising a microemulsion and an active ingredient, wherein the microemulsion comprises a water phase composite, comprising a water solution and a moisturizer; an oil phase composite; and a surfactant composite; and the active ingredient is the substrate of cytochrome P450 3A4 enzyme. The microemulsion of the present invention inhibits the expression of the cytochrome P450 3A4 enzyme so as to improve the efficacy of the active ingredient in the microemulsion mixture. The present invention further provides a method of using the microemulsion mixture, a pharmaceutical microemulsion mixture comprising the microemulsion mixture, and the method for treating psoriasis comprising administering the microemulsion mixture to a subject in need thereof.

19 Claims, 16 Drawing Sheets

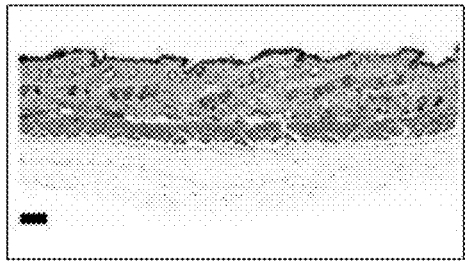
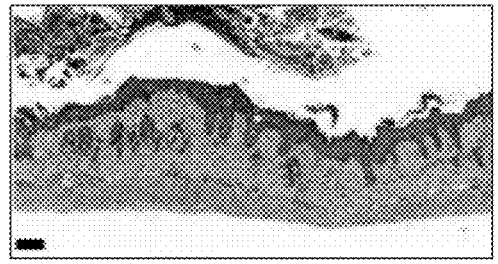
FIG.7A　　　　　　　　FIG.7B
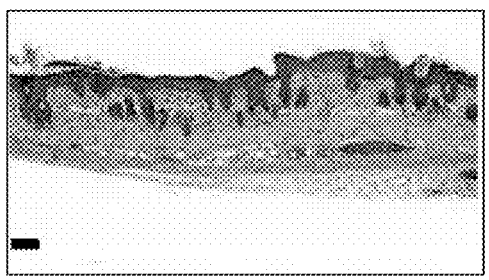
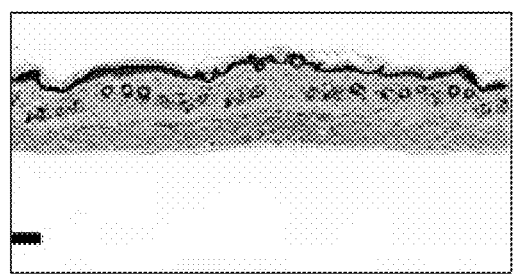
FIG.7C　　　　　　　　FIG.7D
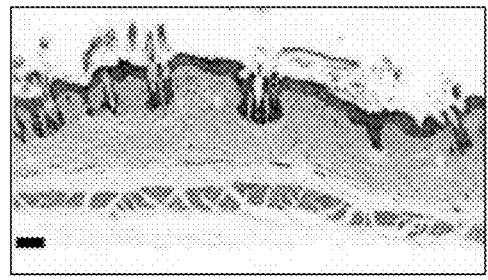
FIG.7E　　　　　　　　FIG.7F

MICROEMULSION MIXTURE AND METHOD OF USING THE SAME, AND PHARMACEUTICAL MICROEMULSION MIXTURE AND METHOD OF USING THE SAME

CROSS-REFERENCE TO RELATED APPLICATION

Pursuant to 35 U.S.C. § 119(a), this application claims the benefits of the priority to Taiwan Patent Application No. 110109930, filed on Mar. 19, 2021, which is incorporated by reference herein in its entirety.

BACKGROUND OF THE INVENTION

1. Field of the Invention

The present invention relates to a microemulsion mixture. The present invention also relates to a method of using the microemulsion mixture, a pharmaceutical microemulsion mixture comprising the microemulsion mixture and desoximetasone, and the method for treating skin diseases.

2. Description of the Prior Arts

Psoriasis, also called silvery scales disease or cattle skin tinea, is a common chronic inflammatory skin disease, but not infectious skin diseases resulting from germ infections. Psoriasis is prone to occur on the scalp, limbs, lower back, ears, finger joints, nails, navel, intergluteal cleft and genitals, and may get widespread all over the body in severe conditions. The histopathological features comprise epidermal hyperproliferation, abnormal keratinocyte differentiation, angiogenesis with blood vessel dilatation, which results in abnormal skin thickening, rough skin, desquamation, red plaques, papules and petechial hemorrhages in patients.

Psoriasis patients often have itchy skin, cracked skin, aches and other ill symptoms. Although such symptoms post no fatal risks, what troubles psoriasis patients the most is their normal social life jeopardized by the ill appearance of the skin, causing the patients' vulnerability to depressed mood, such as social embarrassment, loss of self-esteem, etc. Meanwhile, the emotional stress in turn is one of the factors that induce psoriasis, and makes psoriasis difficult to recover and prone to recurrence.

The current active ingredient in the topical ointments for treating psoriasis comprises: steroids, vitamin A, vitamin D derivatives, coal tar and salicylic acid. However, steroids are only suitable for short-term disease control; vitamin A and salicylic acid may cause skin irritation; a long-term use of vitamin D derivatives may instead cause inflamed and itchy skins; coal tar generally has a pungent smell, and may cause a dry skin and stain the contacted objects, such as furniture, resulting in staining problems and inconvenience for use.

In fact, in addition to psoriasis, there are other skin diseases that cannot be cured permanently; for example, allergic skins may also recur frequently and requires daily and long-term skin care or treatments. Therefore, there is a necessity to develop an active ingredient delivery system that can reduce the dosage of active ingredients or improve its efficacy so as to avoid the risk of side effects resulting from a long-term use of a specific active ingredient or medicament.

SUMMARY OF THE INVENTION

To reach the aforementioned object, the present invention provides a microemulsion mixture, comprising: a microemulsion and an active ingredient, wherein the microemulsion comprises: a water phase composite, comprising a water solution and a moisturizer; an oil phase composite, comprising one selected from silicone oil, squalene, triglyceride and any combination thereof; and a surfactant composite, comprising one selected from polyoxyl hydrogenated castor oil, tween, polyethylene glycol (PEG), propylene glycol (1,2-PG) and any combination thereof; and based on a total amount of the water phase composite, the oil phase composite and the surfactant composite, the water phase composite is in an amount from 25 weight percent to 39 weight percent, the oil phase composite is in an amount from 8 weight percent to 22 weight percent, and the surfactant composite is in an amount from 53 weight percent to 67 weight percent; and the active ingredient is the substrate of cytochrome P450 3A4 enzyme.

The microemulsions of the present invention are vehicles in a micro-emulsified state and serve as an active ingredient delivery system which entraps the active ingredients in the emulsion droplets at micron-scale or nano-scale, wherein the emulsion droplets thereof comprise a water phase composite, an oil phase composite and a surfactant composite. By mixing the three composites at a certain weight ratio, they could form a thermodynamically stable and isotropic mixture spontaneously, and are generally transparent.

For example, based on the total amount of the water phase composite, the oil phase composite and the surfactant composite, the water phase composite is in an amount from 25 weight percent, 26 weight percent, 27 weight percent, 28 weight percent, 29 weight percent, 30 weight percent, 31 weight percent, 32 weight percent, 33 weight percent, 34 weight percent, 35 weight percent, 36 weight percent, 37 weight percent, 38 weight percent, or 39 weight percent.

For example, based on the total amount of the water phase composite, the oil phase composite and the surfactant composite, the oil phase composite is in an amount from 8 weight percent, 9 weight percent, 10 weight percent, 11 weight percent, 12 weight percent, 13 weight percent, 14 weight percent, 15 weight percent, 16 weight percent, 17 weight percent, 18 weight percent, 19 weight percent, 20 weight percent, 21 weight percent, or 22 weight percent.

For example, based on the total amount of the water phase composite, the oil phase composite and the surfactant composite, the surfactant composite is in an amount from 53 weight percent, 54 weight percent, 55 weight percent, 56 weight percent, 57 weight percent, 58 weight percent, 59 weight percent, 60 weight percent, 61 weight percent, 62 weight percent, 63 weight percent, 64 weight percent, 65 weight percent, 66 weight percent, or 67 weight percent.

For further clarification, emulsification is different from microemulsification for the reasons that the emulsions are cloudy products, fundamentally thermodynamically unstable and eventually result in phase separation. Further, emulsions require more energy input than microemulsions during emulsification. Therefore, emulsions and microemulsions are different in three aspects: the thermodynamic stability, appearance and preparation method.

The water phase composite of the present invention comprises a moisturizer, which moisturizes the skin or softens the stratum corneum of the skin so as to facilitate the active ingredient to penetrate across the stratum corneum of the skin.

In one embodiment, the microemulsion or the microemulsion mixture of the present invention is for external use, which is administered to or applied topically to the skin or mucous membranes, such as the site where the skin has hairs or the skin in rugae.

Preferably, the diameter of the emulsion droplets is from 500 nanometers to 900 nanometers, such as 500 nanometers, 600 nanometers, 700 nanometers, 800 nanometers or 900 nanometers. More preferably, the diameter thereof is from 690 nanometers to 700 nanometers.

Preferably, the polydispersity index of the distribution of the emulsion droplets is 0.43 to 0.44. More preferably, the polydispersity index thereof is 0.435.

Preferably, the Zeta potential of the microemulsion is −14 mV to −16 mV. More preferably, the Zeta potential thereof is −14.5 mV to −15.45 mV.

Preferably, the viscosity of the microemulsion is 3000 cP to 3200 cP. More preferably, the viscosity thereof is 3100 cP to 3120 cP.

Preferably, the electronic conductivity of the microemulsion is 20 μS/cm to 30 μS/cm. More preferably, the electronic conductivity thereof is 23.65 μS/cm to 24.65 μS/cm.

Preferably, the microemulsion is both oil-in-water and water-in-oil microemulsions and defined as a bicontinuous microemulsion. As the microemulsion of the present invention is a bicontinuous microemulsion, both oil-in-water and water-in-oil microemulsions coexist so as to facilitate the efficacy preservation of the active ingredients and enhance the skin penetration rate of the active ingredients.

Preferably, based on the total amount of the water phase composite, the oil phase composite and the surfactant composite, the water phase composite is in an amount from 25 weight percent to 35 weight percent, the oil phase composite is in an amount from 8 weight percent to 12 weight percent, and the surfactant composite is in an amount from 53 weight percent to 67 weight percent.

Preferably, the water solution is an isotropic solution, and based on the total amount of the water phase composite, the isotropic solution is in an amount of at least 30 weight percent.

Preferably, the moisturizer comprises sorbitol, and based on the total amount of the water phase composite, the sorbitol is in an amount of at least 40 weight percent.

Preferably, the moisturizer comprises glycerol, and based on the total amount of the water phase composite, the glycerol is in an amount of at least 10 weight percent.

Preferably, the water solution is an isotropic solution, and the moisturizer comprises the sorbitol and the glycerol, and based on the total amount of the isotropic solution, sorbitol and glycerol, the isotropic solution is in an amount from 31 weight percent to 39 weight percent, the sorbitol is in an amount from 45 weight percent to 55 weight percent, and the glycerol is in an amount from 12 weight percent to 18 weight percent.

For example, based on the total amount of the isotropic solution, the sorbitol and the glycerol, the isotropic solution is in an amount of 31 weight percent, 33 weight percent, 35 weight percent, 37 weight percent, or 39 weight percent; the sorbitol is in an amount of 45 weight percent, 47 weight percent, 49 weight percent, 51 weight percent, 53 weight percent, or 55 weight percent; and the glycerol is in an amount of 12 weight percent, 13 weight percent, 14 weight percent, 15 weight percent, 16 weight percent, 17 weight percent, or 18 weight percent.

More preferably, the isotropic solution is PBS buffer.

In one embodiment, the PBS buffer comprises 0.01 M phosphate buffer, 0.0027 M potassium chloride and 0.137 M sodium chloride, and the pH of the PBS buffer is 7.4 at 25° C.

Preferably, the oil phase composite comprises silicone oil, and based on the total amount of the oil phase composite, the silicone oil is in an amount of at least 60 weight percent. Preferably, the silicone oil is in an amount from 65 weight percent to 77 weight percent.

Preferably, the oil phase composite comprises silicone oil, squalene and triglyceride, and based on the total amount of the oil phase composite, the silicone oil is in an amount from 65 weight percent to 77 weight percent, such as 65 weight percent, 68 weight percent, 71 weight percent, 74 weight percent or 77 weight percent; the squalene is in an amount from 3 weight percent to 11 weight percent, such as 3 weight percent, 5 weight percent, 7 weight percent, 9 weight percent, or 11 weight percent; and the triglyceride is in an amount from 15 weight percent to 27 weight percent, such as 15 weight percent, 18 weight percent, 21 weight percent, 24 weight percent, or 27 weight percent.

Preferably, the oil phase composite comprises silicone oil, squalene and triglyceride, and the weight ratio of the silicone oil, the squalene and the triglyceride is 8 to 12:0.8 to 1.2:2.5 to 3.5.

For example, the weight ratio of the silicone oil, the squalene and the triglyceride is 8, 9, 10, 11, or 12:0.8, 0.9, 1.0, 1.1, or 1.2:2.5, 2.7, 2.9, 3.1, 3.3, or 3.5.

More preferably, the viscosity of the silicone oil at 25° C. is from 180 mPa·s to 220 mPa·s, such as 180 mPa·s, 190 mPa·s, 200 mPa·s, 210 mPa·s, or 220 mPa·s.

Preferably, the surfactant composite comprises polyoxyl hydrogenated castor oil, and based on the total amount of the surfactant composite, the polyoxyl hydrogenated castor oil is in an amount of at least 60 weight percent. Preferably, the surfactant composite comprises polyoxyl hydrogenated castor oil, tween, PEG, and 1,2-PG, and based on the total amount of the surfactant composite, the polyoxyl hydrogenated castor oil is in an amount from 70 weight percent to 85 weight percent, such as 70 weight percent, 74 weight percent, 78 weight percent, 82 weight percent, or 85 weight percent; and each of the tween, the PEG, and the 1,2-PG is in an amount from 5 weight percent to 10 weight percent, respectively, such as 5 weight percent, 6 weight percent, 7 weight percent, 8 weight percent, 9 weight percent, or 10 weight percent.

Preferably, the surfactant composite comprises polyoxyl hydrogenated castor oil, tween, PEG, and 1,2-PG, and the weight ratio of the polyoxyl hydrogenated castor oil, the tween, the PEG, and the 1,2-PG is 8 to 12:0.8 to 1.2:0.8 to 1.2:0.8 to 1.2.

For example, the weight ratio of the polyoxyl hydrogenated castor oil, the tween, the PEG, and the 1,2-PG is 8, 9, 10, 11 or 12:0.8, 0.9, 1.0, 1.1 or 1.2:0.8, 0.9, 1.0, 1.1 or 1.2:0.8, 0.9, 1.0, 1.1 or 1.2.

The polyoxyl hydrogenated castor oil is also called hydrogenated castor oil.

Preferably, the polyoxyl hydrogenated castor oil is polyoxyl 40 hydrogenated castor oil, also called polyoxyethylene castor oil, Kolliphor® RH 40, Cremophor RH 40, macrogolglycerol hydroxystearate 40, polyethylene glycol (PEG)-40 castor oil, PEG-40 hydrogenated castor oil, and PEG40 hydrogenated castor oil.

Preferably, the tween is tween 80.

Preferably, the PEG is PEG 400.

According to the present invention, the microemulsion enhances the skin penetration rate of the active ingredients and/or bioavailability thereof.

According to the present invention, the microemulsion ameliorates abnormal transepidermal water loss and enhances or restores skin hydration. The present invention also provides a method for moisturizing skin or softening the stratum corneum of the skin, comprising topically administering to a subject in need thereof an effective amount of the microemulsion.

The cytochromes P450 3A4 enzyme, abbreviated to CYP3A4, is an oxidative enzyme and takes part in the biotransformation and metabolism of various active ingredients. For example, CYP3A4 takes part in the biotransformation and metabolism of about 30% medicaments. According to the present invention, the microemulsion inhibits the expression of CYP3A4. Preferably, the microemulsion inhibits the expression of CYP3A4 in skin or mucous membranes. More preferably, the expression of CYP3A4 is enhanced in irritated or abnormal skins or mucous membranes.

The substrate of cytochrome P450 3A4 enzyme indicates that CYP3A4 takes part in the biotransformation and metabolism of the active ingredients, and is not limited to the scenario of a direct contact or a direct combination between the active ingredient and CYP3A4.

Preferably, the substitute group of the active ingredient comprises, but is not limited to, one selected from keto, aryl, heteroaryl and any combination thereof.

Preferably, based on the total amount of the microemulsion mixture, the effective or safe concentration of the active ingredient is 0.005 weight percent to 0.25 weight percent, such as 0.005 weight percent, 0.01 weight percent, 0.03 weight percent, 0.05 weight percent, 0.07 weight percent, 0.1 weight percent, 0.13 weight percent, 0.15 weight percent, 0.17 weight percent, 0.2 weight percent, 0.23 weight percent, or 0.25 weight percent. The "safe concentration" or "effective concentration" indicates that the benefit derived from the use of the active ingredient in such specified concentration outweighs the risk thereof, which warrants the legitimacy of the use in such specified concentration on humans.

The present invention further provides a method for improving the efficacy of skin care, comprising administering to a subject in need thereof an effective amount of the microemulsion mixture or the pharmaceutical microemulsion mixture. Preferably, "improving the efficacy of skin care" means improving skin conditions.

More preferably, the active ingredient is not classified as drug according to Federal Food, Drug, and Cosmetic Act. Further preferably, the active ingredient is classified as food or cosmetic.

The present invention further provides a pharmaceutical microemulsion mixture, comprising the aforementioned microemulsion mixture, wherein the substrate of cytochrome P450 3A4 enzyme comprises a therapeutically effective concentration of desoximetasone (DXM).

Preferably, based on the total amount of the pharmaceutical microemulsion mixture, the therapeutically effective concentration of desoximetasone is 0.005 weight percent to 0.25 weight percent, such as 0.005 weight percent, 0.01 weight percent, 0.03 weight percent, 0.05 weight percent, 0.07 weight percent, 0.1 weight percent, 0.13 weight percent, 0.15 weight percent, 0.17 weight percent, 0.2 weight percent, 0.23 weight percent, or 0.25 weight percent.

The present invention further provides a medicament for children or adolescents, comprising an effective amount of the pharmaceutical microemulsion mixture. Preferably, the concentration of desoximetasone is 0.005 weight percent to 0.05 weight percent. As mentioned above, the microemulsion of the present invention mixed with a significantly lowered concentration of desoximetasone than that of the commercial desoximetasone medicament still demonstrates better therapeutic efficacy, so such pharmaceutical microemulsion mixture warrants its use in younger population, and could serve as a medicament for children or adolescents. The medicament for children or adolescents indicates that such medicament is suitable for the populations at the age from 0 year old to 18 years old, such as infants, babies, children or adolescents. Preferably, the medicament for children or adolescents is administered to a subject at the age older than 0 year old and younger than 18 years old.

In one embodiment, the microemulsion mixture or the pharmaceutical microemulsion mixture is administered to a subject at the age older than 0 year old and younger than 18 years old.

The present invention further provides a method for inhibiting the expression of proliferating cell nuclear antigen (PCNA), comprising administering to a subject in need thereof an effective amount of the pharmaceutical microemulsion mixture.

The present invention further provides a method for treating, ameliorating or easing a skin symptom resulting from skin inflammation, comprising administering to a subject in need thereof an effective amount of the pharmaceutical microemulsion mixture. Preferably, the skin symptom resulting from skin inflammation comprises one selected from dry skin, epidermal acanthosis, parakeratosis, tortuous capillary dilatation in papillary dermis, erythema, inflammatory cell infiltration, epidermal hyperproliferation, abnormal keratinocyte differentiation, angiogenesis with blood vessel dilatation, abnormal skin thickening, rough skin, desquamation, red plaques, papules, petechial hemorrhages and any combination thereof.

The present invention further provides a method for treating, ameliorating or easing a skin symptom resulting from autoimmunity, comprising administering to a subject in need thereof an effective amount of the pharmaceutical microemulsion mixture.

The present invention further provides a method for treating, ameliorating or easing psoriasis, comprising administering to a subject in need thereof an effective amount of the pharmaceutical microemulsion mixture.

The present invention further provides a method for improving or restoring skin barrier functions or skin hydration, reducing abnormal transepidermal water loss, or ameliorating erythema or abnormal epithelial cell proliferations, comprising administering to a subject in need thereof an effective amount of the pharmaceutical microemulsion mixture, wherein the subject has injured skin or skin inflammation.

The "therapeutically effective concentration" of DXM or the "effective amount" of the pharmaceutical microemulsion mixture indicates that a concentration or an amount thereof demonstrates the efficacies of (1) inhibiting the expression of proliferating cell nuclear antigen (PCNA); (2) treating, ameliorating or easing psoriasis or a skin symptom resulting from skin inflammation or autoimmunity; or (3) improving or restoring skin barrier functions or skin hydration, reducing abnormal transepidermal water loss, or ameliorating erythema or abnormal epithelial cell proliferations in a subject, and the subject has injured skin or skin inflammation.

The present invention further provides a method for preventing, treating or ameliorating skin cancer, comprising administering to a subject in need thereof an effective amount of the microemulsion mixture. Preferably, the substrate of cytochrome P450 3A4 enzyme comprises one selected from everolimus, ibrutinib, idelalisib, crizotinib, imatinib, ivacaftor, enzalutamide, mitotane and any combination thereof.

The present invention further provides a method for preventing, treating or ameliorating inflammation, comprising administering to a subject in need thereof an effective amount of the microemulsion mixture. Preferably, the substrate of cytochrome P450 3A4 enzyme comprises one selected from ebastine, budesonide and the combination thereof.

In one embodiment, the inflammation is skin inflammation.

The present invention further provides an antibacterial or antifungal method, comprising administering to a subject in need thereof an effective amount of the microemulsion mixture. Preferably, the substrate of cytochrome P450 3A4 enzyme comprises one selected from erythromycin, rifampicin, clarithromycin, itraconazole, fluconazole, itraconazole, ketoconazole, posaconazole, telithromycin, troleandomycin, voriconazole, ciprofloxacin, clotrimazole and any combination thereof.

In one embodiment, the antibacterial or antifungal method is skin antibacterial or antifungal method.

To sum up, the microemulsion of the present invention per se has the following advantages: (1) preserving the stability of the active ingredient; (2) enhancing the skin penetration rate of the active ingredients and/or bioavailability thereof; (3) moisturizing skin or softening the stratum corneum of the skin; (4) inhibiting the expression of P450 3A4; and (5) having extremely low irritation and sensitization potential for the injured or inflamed skin. Therefore, the microemulsion of the present invention can serve as the vehicle of daily skin care products, which provides another safer and more effective option for consumers with problematic skin. Further, the microemulsion mixture of the present invention can be used by the subject having sensitive, injured or inflamed skin for daily skin care.

Finally, the microemulsion of the present invention is further mixed with desoximetasone (DXM) to obtain a pharmaceutical microemulsion mixture, which has the following efficacies: (1) inhibiting abnormal epithelial cell proliferations; (2) treating, ameliorating or easing psoriasis or a skin symptom resulting from skin inflammation or autoimmunity; (3) lowering the required therapeutically effective concentration, whereas improving the therapeutic efficacy; (4) serving as a medicament for children or adolescents; and (5) improving or restoring skin barrier functions or skin hydration, reducing abnormal transepidermal water loss, or ameliorating erythema, and provides a new option of topical use dosage form for patients with injured skin or skin inflammation, which facilitates lowering the risk of side effects resulting from a long-term use of medicaments and enhancing therapeutic efficacy.

BRIEF DESCRIPTION OF THE DRAWINGS

FIGS. 7A to 7F are the photographs of the histological sample sections of mice skin stained with hematoxylin and eosin in Experiment 6.

DETAILED DESCRIPTION OF THE PREFERRED EMBODIMENTS

The present invention is further explained through the following embodiments. A person having ordinary skill in the art can easily understand the advantages and efficacies achieved by the present invention. The present invention should not be limited to the contents of the embodiments. A person having ordinary skill in the art can make some improvement or modifications which are not departing from the spirit and scope of the present invention to practice or apply the content of the present invention.

Preparation 1: Construction of Pseudo Ternary Phase Diagram

For determination of the existence zone of microemulsions, the pseudo ternary phase diagrams were constructed by using aqueous titration method at room temperature in this experiment. The ingredients comprised a water phase composite, an oil phase composite and a surfactant composite; wherein the water phase composite comprised PBS buffer, sorbitol and glycerol, and based on the total amount of the PBS buffer, sorbitol and glycerol, the PBS buffer was in an amount of 35 weight percent, sorbitol was in an amount of 50 weight percent, and glycerol was in an amount of 15 weight percent; the oil phase composite comprised silicone oil AR200, squalene and triglyceride, and the weight ratio of silicone oil AR200, squalene and triglyceride was 10:1:3; the surfactant composite comprised Cremophor RH 40, tween 80, PEG 400 and 1,2-PG, and the weight ratio of Cremophor RH 40, tween 80, PEG 400 and 1,2-PG was 10:1:1:1. All the ingredients were purchased from Merck KGaA.

The oil phase composite and the surfactant composite were mixed in a weight ratio of 1:9, 2:8, 3:7, 4:6, 5:5, 6:4, 7:3, 8:2 and 9:1, respectively to obtain various first mixtures for titration. The water phase composite was added into each of the first mixtures to obtain a second mixture until such second mixture turned turbid, and the amount of the water phase composite used was recorded. Afterwards, the weights of the water phase composite, the oil phase composite and the surfactant composite in each of the various second mixtures were used to construct a pseudo ternary phase diagram (as shown in FIG. 1); wherein the area on the right side of the line with black spots represented the existence zone of microemulsions, and the formulation within such area formed transparent solutions without phase separation of different ingredients, whereas the formulations in the area on the left side of the line with black spots represented such formulations failed to form microemulsions.

Preparation 2: Microemulsions

Figure 1:
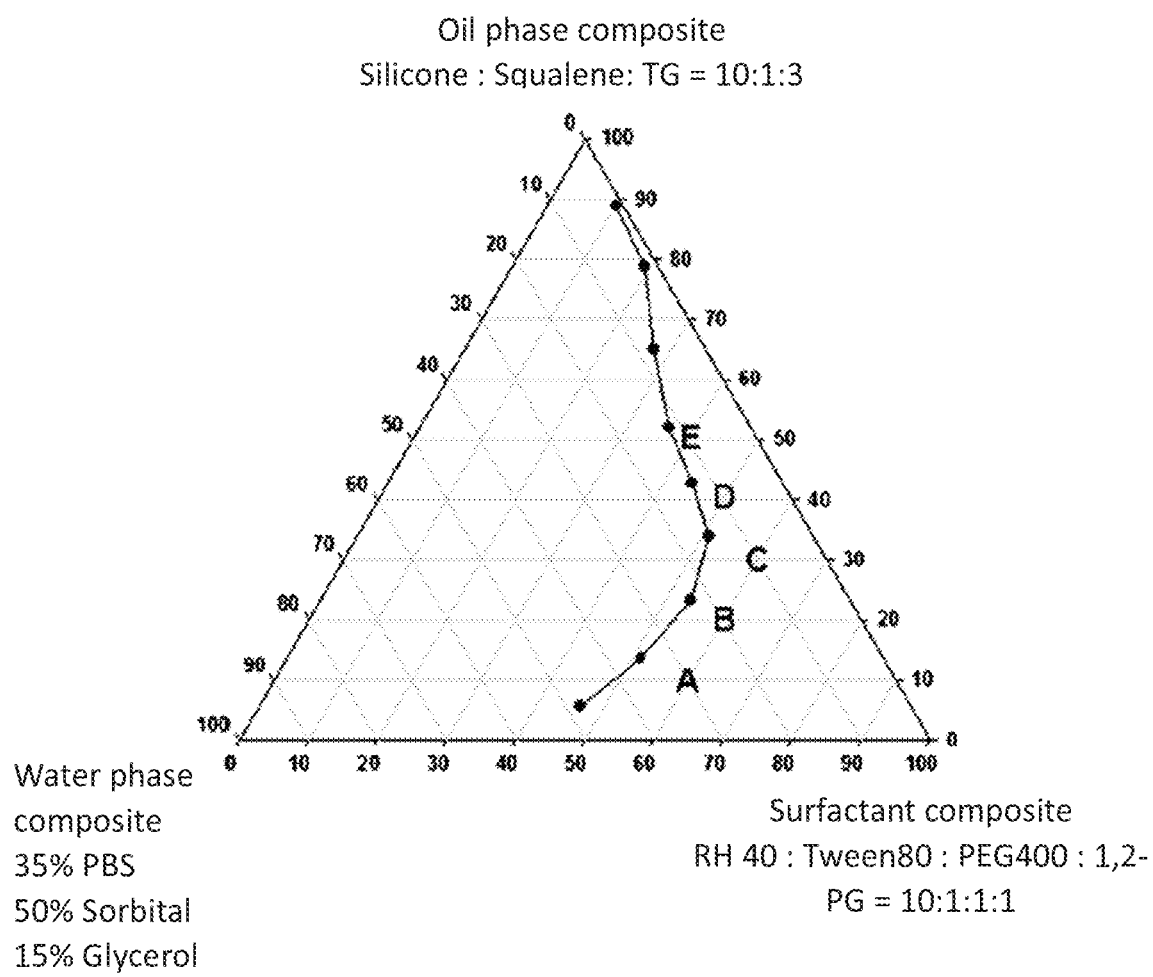
FIG. 1 is the pseudo ternary phase diagram showing the existence zone of microemulsions.
Figure 2A:
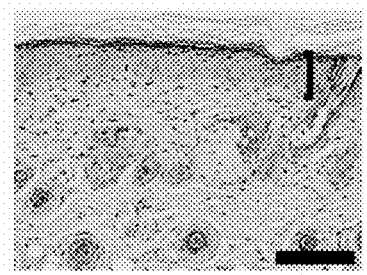
FIGS. 2A to 2F are the histological staining sample sections of mice skin in the skin irritation test.
Figure 2B:
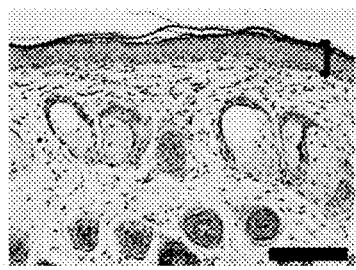
Figure 2C:
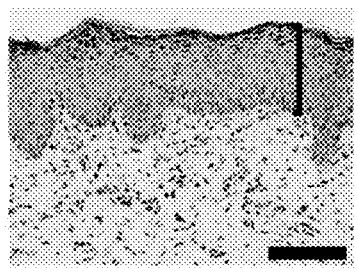
Figure 2D:
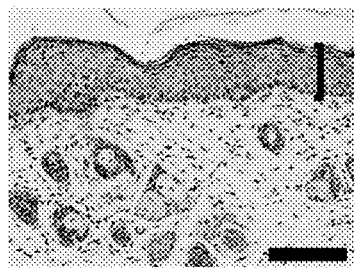
Figure 2E:
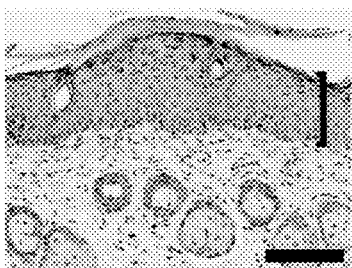
Figure 2F:
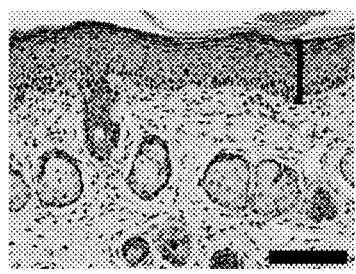

Five microemulsions were prepared according to the formulations of spot A to spot E in FIG. 1 as shown in Table 1.

TABLE 1

Formulations of the microemulsions

| Group | Water phase composite (wt %) | Oil phase composite (wt %) | Surfactant composite (wt %) |
| --- | --- | --- | --- |
| A | 30 | 10 | 60 |
| B | 20 | 20 | 60 |
| C | 10 | 30 | 60 |
| D | 10 | 40 | 50 |
| E | 10 | 50 | 40 |

The aforementioned weight percentage (wt %) was based on the total amount of the water phase composite, the oil phase composite and the surfactant composite, and the weight percentages of the three composites were 100 weight percent in total.

Materials:

(1) Experimental Animals

Male BALB/c mice (6 to 8 weeks old, National Laboratory Animal Center, Tainan, Taiwan) were housed under conditions of controlled humidity (40%) and temperature (24±2° C.), with a 12-hour light-dark cycle in this experiment. All animal experiments were conducted in accordance with accepted standards of humane animal care, under protocols approved by the Institutional Animal Care and Use Committee (IACUC) of Cathay General Hospital.

(2) The Preparation of Mice Skin:

Normal untreated mice were sacrificed after anesthesia and the full-thickness dorsal skin thereof was excised. Further, the hairs on the full-thickness dorsal skin were firstly removed by using a depilatory cream (Nair, Church & Dwight Co., Inc., Ewing, NJ, USA), and the subcutaneous tissue was then surgically removed to obtain mice skin. The mice skin was washed with distilled water for immediate use in the following experiments.

Experiment 1: Skin Irritation Test

There were four mice in each of the control group and 5 experimental groups in this experiment. From Day 0, a daily topical application of Imiquimod (IMQ) cream for 6 consecutive days was provided to each group to induce psoriasis symptoms. Afterwards, the control group received no treatment in the following 5 consecutive days, whereas the 5 experimental groups received a daily topical application of the microemulsions of Formulation A to Formulation E, respectively. All mice were sacrificed on Day 11, and the skin samples thereof were fixed in 10% formalin. After embedding, histological staining sample sections were prepared to observe which group showed the least skin irritation response, and the experimental results were shown in FIGS. 2A to 2F, wherein the black line at the bottom in each figure was a scale bar representing 100 μm, and the bracket indicated the thickness of epidermis.

FIGS. 2A to 2F sequentially showed the experimental results of the control group and the 5 experimental groups receiving the microemulsions of Formulation A to Formulation E, respectively. According to FIGS. 2A to 2F, the experimental results of both the control group and the experimental group receiving the microemulsion of Formulation A were the most similar, and the microemulsion of Formulation A resulted in the least degree of epidermal thickening, which indicates that the microemulsion of Formulation A was least irritant to the mice skin.

While surfactants generally irritate skins, the experimental results showed that the microemulsion of Formulation A with higher amount of the surfactant composite than those of both Formulations D and E resulted in less irritation response, such less irritation response of the microemulsion of Formulation A constituted unexpected efficacy.

Experiment 2: Stability Test of the Microemulsion

The microemulsion of Formulation A was subjected to the centrifugation test to evaluate its physical stability and stress test to evaluate its thermodynamic stability. In the centrifugation test, the microemulsion of Formulation A was centrifuged at 3500 rpm for 30 minutes. In the stress test, the microemulsion of Formulation A was first stored at 4° C. for 48 hours and then 45° C. for 48 hours, and the storages in both degrees were repeated for a period of six cycles. Further, the microemulsion of Formulation A was stored at 25° C. for 48 hours and then −21° C. for 48 hours, and the storages in both degrees were repeated for a period of three cycles. After the tests, the microemulsion of Formulation A showed no phase separation, so the microemulsion of Formulation A had good stability.

Experiment 3: The Character Analysis for the Microemulsions (1) Measurement of Droplet Size (Diameter) and Zeta ($\zeta$) Potential The droplet size and zeta potential of the microemulsion of Formulation A were measured by a Nanoparticle Analyzer (SZ-100, Horiba Ltd., Kyoto, Japan) at a scattering angle of 90° under ambient conditions. Both measurements were repeated three times and the results were shown in Table 2.

(2) Measurement of Electronic Conductivity

The electronic conductivity of the microemulsion of Formulation A was measured by a conductivity meter (Eutech COND 6+, Eutech Instruments Pte Ltd., ThermoFisher Scientific, Singapore, Singapore) under ambient conditions. The measurement were repeated three times and the result was shown in Table 2.

(3) Measurement of Viscosity

The viscosity of the microemulsion of Formulation A was measured by a Visco-895 Viscometer (Atago Co., Inc., Tokyo, Japan) using spindle A3 RE-77106 at room temperature, and the result was shown in Table 2.

TABLE 2 the physicochemical properties of the microemulsion of Formulation A

| Properties (Unit) | The microemulsion of Formulation A |
| --- | --- |
| Droplet size (nm) | 696.2 ± 188.3 |
| Size distribution (PI) | 0.435 ± 0.004 |
| Zeta ($\zeta$) potential (mV) | −14.95 ± 0.64 |
| Viscosity (cP) | 3112.3 ± 5.8 |
| Electronic conductivity (μS/cm) | 24.15 ± 0.07 |

The PI in Table 2 stands for polydispersity index.

According to Table 2, the droplet size of the microemulsion of Formulation A was in nano scale so as to enhance the skin penetration rate of the microemulsion; Zeta ($\zeta$) potential is an essential index of stability of the suspension. The greater the absolute zeta potential, the higher the stability of colloidal dispersions. Besides, the microemulsion with a conductivity ranging from 10.3 μS/cm to 52.5 μS/cm can be defined as a bicontinuous microemulsion, in which both oil-in-water and water-in-oil microemulsions coexist. As the microemulsion of Formulation A had a conductivity of about 24 μS/cm and could be characterized as a bicontinuous microemulsion, the oil-in-water microemulsion in the microemulsion of Formulation A could enhance the skin penetration rate of the active ingredients, and the water-in-oil microemulsion could lower the skin irritation potential of the vehicles. In other words, the microemulsion of Formulation A was especially suitable for injured or inflamed skin.

Experiment 4: The Expression Assessment Test of CYP3A4

Materials:

(1) Experimental Animals

Male BALB/c mice (6 to 8 weeks old, BioLASCO Taiwan Co., Ltd) were housed under conditions of controlled humidity (40%) and temperature (22±2° C.), with a 12-hour light-dark cycle in this experiment. All animal experiments were conducted in accordance with accepted standards of humane animal care, under protocols approved by the Institutional Animal Care and Use Committee (IACUC) of Cathay General Hospital.

(2) Experimental procedure: This experiment included three groups: the normal group, the control group and the vehicle group, and each group had 4 mice. The normal group received no experimental treatment. In both the control group and the vehicle group, psoriasis was induced by following a standard protocol published in the journal article on Scientific Reports: "Methodological refinement of Aldara-induced psoriasiform dermatitis model in mice", and the steps were as follows: First, the dorsal skin of the aforementioned male BALB/c mice (6 to 8 weeks old) was shaved and administered with a daily topical application of 62.5 mg ALDARA CREAM 5% (Aldara, 3M Pharmaceuticals, Saint Paul, MN, USA), which contained a daily dose of 3.125 mg IMQ, on Day 0 for six consecutive days. During the six consecutive days, the vehicle group received further treatment: After three to four hours of IMQ application, the mice further received a daily topical application of 100 μL microemulsion of Formulation A, whereas the control group received no further treatment. All three groups were sacrificed on Day 6 to obtain mice skin specimens. During the experimental period, each mouse was housed in a separate cage to prevent activities between mice that could affect skin integrity; meanwhile, each individual mouse was provided with toys such as wooden bars to comply with IACUC regulations.

(3) Immunohistochemical Staining for CYP3A4 in Mice Skin

The mice skin specimens of the three groups were fixed in 10% formalin solution and embedded in paraffin after routine treatments. Sections of 5 μm thickness were cut, incubated with primary antibodies against CYP3A4 (Proteintech Group, Inc.), incubated with second antibodies and stained by using a Ventana BenchMark XT automated stainer (Ventana Medical Systems, Inc.). The steps were as follows: The sections were incubated with the primary antibody for 60 minutes at 37° C., and then the incubation continued overnight at 4° C. to obtain incubated sections. Subsequently, by using an ultraView Universal DAB Detection kit (Catalogue No. 760-500, Mixture of mouse and rabbit origins, Ventana Medical Systems Inc.), the incubated sections were further incubated with the secondary biotinylated antibody for 1 hour at room temperature to obtain sample sections, and then the levels of diaminobenzidine (DAB) were visualized for quantification Finally, the sample sections were counterstained with hematoxylin, and examined under an optical microscope (BX41; Olympus Corporation). The immunostaining results of the normal group, the control group and the vehicle group were sequentially shown in FIGS. 3A to 3C, wherein the black line at the bottom in each figure was a scale bar representing 100 μm.

Figure 3A:
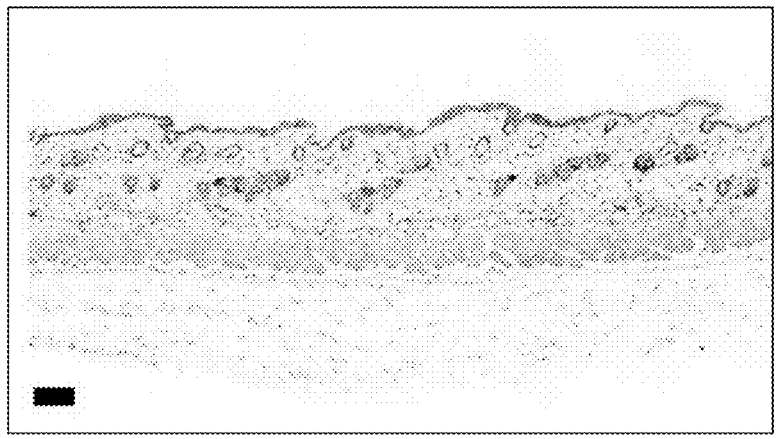
FIGS. 3A to 3C are immunohistochemical staining photographs for CYP3A4 of the histological sample sections of mice skin.
Figure 3B:
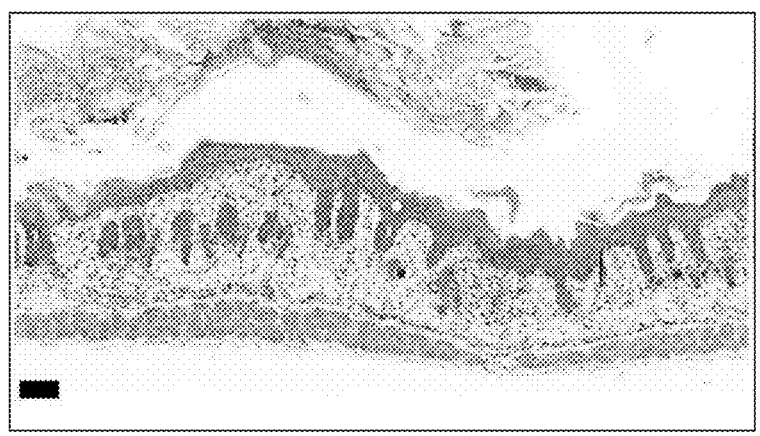
Figure 3C:
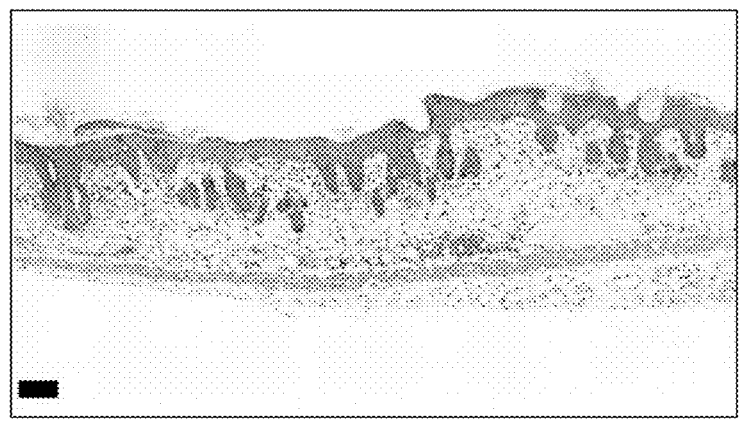

According to FIGS. 3A to 3C, in comparison with the normal group in FIG. 3A, both the control group in FIG. 3B and the vehicle group in FIG. 3C were topically applied with IMQ, so the epidermis of both groups were significantly thickened. Besides, the control group was not further provided with the microemulsion of Formulation A, and showed a desquamation in a state that is more severe than that of the vehicle group. Therefore, FIG. 3B showed desquamating fragments in the upper part of the photograph in addition to the epidermal thickening issue.

(4) Immuno-Intensity Counting for Immunohistochemical Staining for CYP3A4 in Mice Skin The skin tissues on the slides after the aforementioned immunohistochemical staining were scanned by using a slide scanner (3DHISTECH Kft.) at a magnification of ×200, and then CellQuant and PatternQuant softwares (3DHISTECH Kft.) were used for computation. The steps were as follows: Each skin tissue had an assigned annotation region, which was 1 mm wide, reaching the muscle layer to cover the whole thickness of the skin. PatternQuant was programmed to recognize regions of interest, and CellQuant was used to evaluate the H-Score. The H-score was defined in terms of its immune-intensity, and this was then multiplied by the staining percentage to obtain the expression intensity of CYP3A4, giving a range from 0 AU to 300 AU. The immuno-intensity was recorded as 0 for no staining, 1 for faint staining, 2 for moderate staining, and 3 for intense staining, whereas the staining percentage was recorded from 0% to 100%. The immune-intensity and staining percentages were both determined by computation, as calculated by CellQuant, and counting was only permitted within the regions of interest recognized by PatternQuant.

Figure 4:
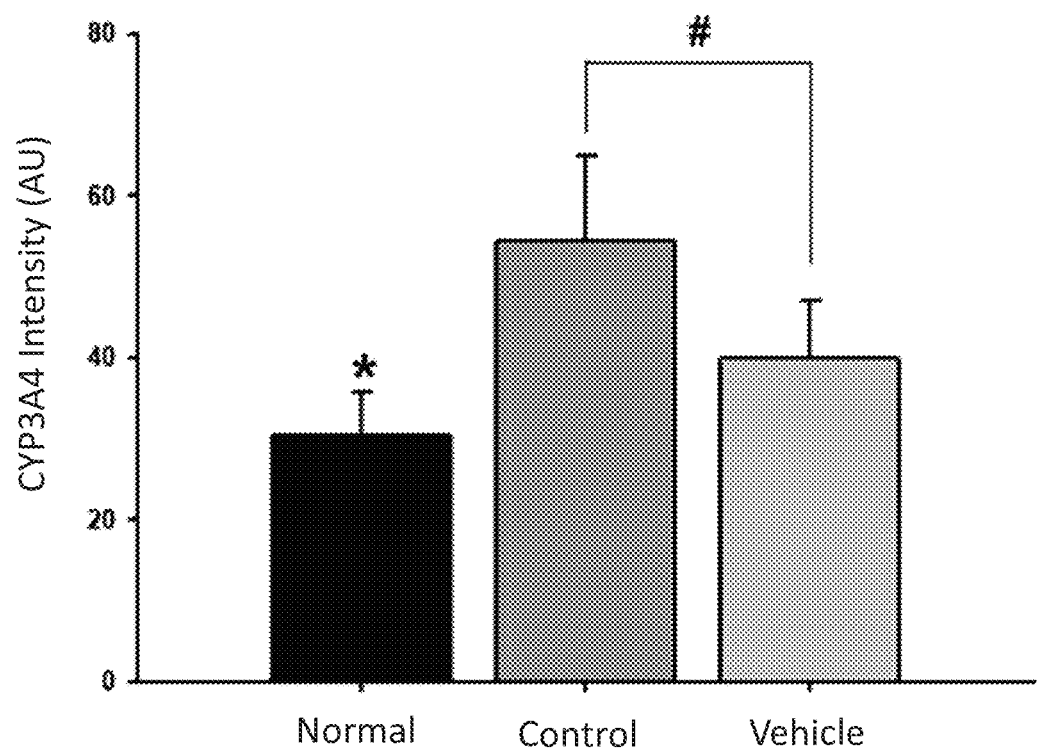
FIG. 4 is a diagram showing the comparison results of the expression assessment test of CYP3A4.

One-way ANOVA followed by Scheffe post hoc test was performed by using SPSS 20 software for statistical analysis of the H-score data, and the result was shown in FIG. 4, wherein * represented that the difference of the data of the normal group was considered statistically significant in comparison with those of the control group and the vehicle group, respectively, and P<0.05; whereas # represented that the difference of the data of the control group was considered statistically significant in comparison with that of the vehicle group, and P<0.05.

According to FIG. 4, the CYP3A4 expression intensity of the normal group was about 30 AU, and that of the control group was about 55 AU, which indicated that the skin irritated by IMQ significantly enhanced the expression of CYP3A4 enzyme. Besides, the CYP3A4 expression intensity of the vehicle group was about 40 AU, which was significantly higher than that of the normal group but significantly lower than that of the control group. Therefore, the microemulsion of Formulation A indeed can inhibit the expression of CYP3A4 enzyme or lower the enhanced expression of CYP3A4 enzyme resulting from the irritation by IMQ so as to prevent the active ingredients being oxidized or degraded by the CYP3A4 enzyme, or prevent lowering the oxidation or degradation rate of the active ingredients.

Experiment 5: Skin Barrier Function Assessment Test

There are six groups in this experiment as shown in Table 3, and the experimental animals and the experimental procedures were the same as Experiment 4.

TABLE 3 the groups in the skin barrier function assessment test

| Group | Experimental procedures |
|---|---|
| The normal group | No treatment |
| The control group | a daily dose of 3.125 mg IMQ |
| The vehicle group | a daily dose of 3.125 mg IMQ followed by a daily dose of 100 μL microemulsion of Formulation A |
| The H.DXM group | a daily dose of 3.125 mg IMQ followed by a daily dose of 100 μL microemulsion mixture comprising the microemulsion of Formulation A and 0.05% Desoximetasone (DXM) |
| The Chemin group | a daily dose of 3.125 mg IMQ followed by a daily dose of 60 mg Chemin oint (0.25% Desoximetasone ointment, Hua-***, Taiwan) |
| The Esperson group | a daily dose of 3.125 mg IMQ followed by a daily dose of 60 mg Esperson ointment (0.25% DXM) |

The transepidermal water loss (TEWL), skin hydration, and skin erythema values were measured on the dorsal surface of the mice in each group in Table 3 by using an MPA 2 system equipped with Tewameter TM300, Corneometer CM825, and Mexmeter MX18 probes (Courage and Khazaka, Klön, Germany) on Day 0 (before any treatment), Day 3 and Day 6, respectively. The measurement results on Day 6 were shown in FIGS. 5A to 5C, wherein * represented that the normal group was in comparison with all the other groups, and P<0.05; + represented that the Esperson group was in comparison with all the other groups, and P<0.05; and # represented that the H.DXM group was in comparison with all the other groups, and P<0.05.

(1) Transepidermal Water Loss Values Analysis

Figure 5A:
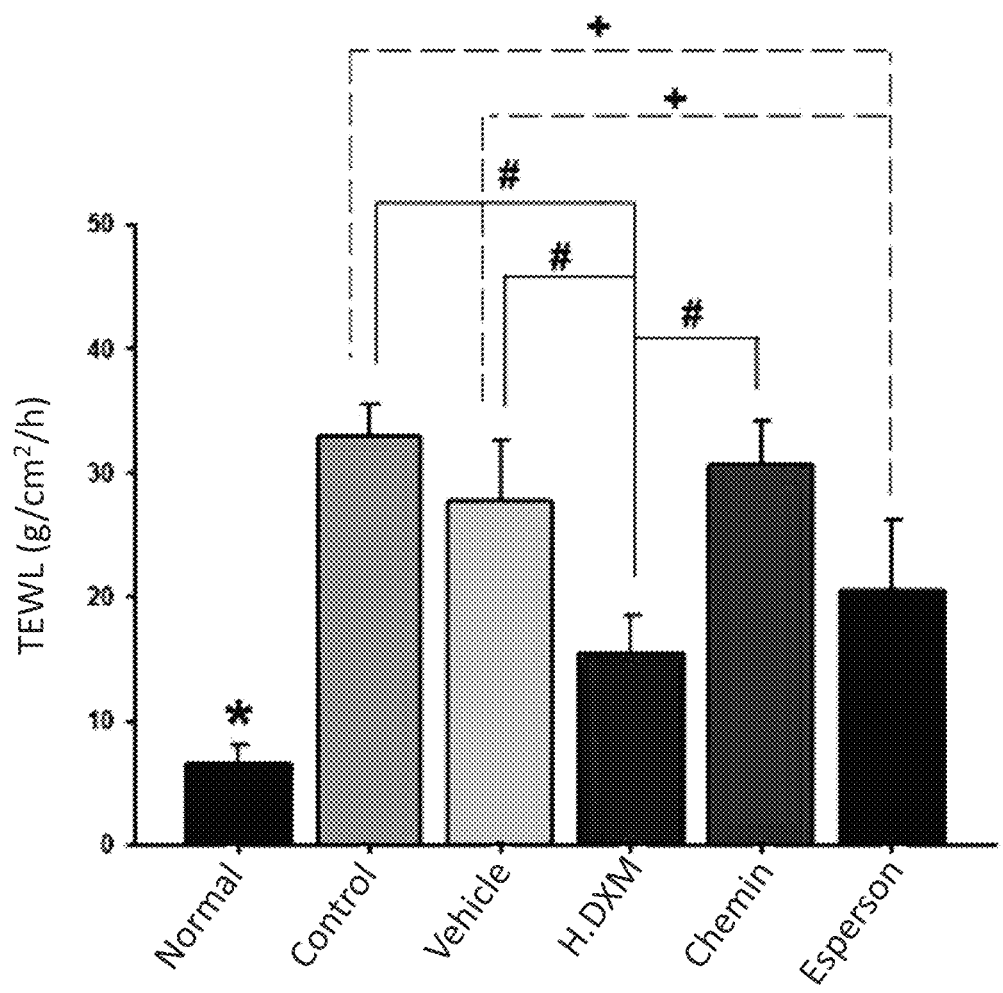
FIGS. 5A to 5C are diagrams showing the comparison results of transepidermal water loss, skin hydration and skin erythema values in the skin barrier function assessment test.

First, as shown in FIG. 5A, the normal group was not topically administered with IMQ, so the skin thereof was in a good condition and the TEWL value was extremely low and lower than 10 $g/m^2/h$. In comparison, the control group was topically administered with IMQ to induce the skin abnormal state like psoriasis, so the TEWL value thereof was relatively high and higher than 30 $g/m^2/h$.

Second, although the Chemin group comprised 0.25% desoximetasone (DXM), the TEWL value thereof was still relatively high and was about 30 $g/m^2/h$. The reason for such unideal result may be the ingredients thereof comprised unknown excipient ingredients, Triethanolamine (TEA) or Aluminum stearate with the molecular weight of 877.4, which was too big to penetrate the skin and accumulated on the skin, which irritated the skin.

Third, the vehicle group did not comprise DXM, and the TEWL value thereof was lower than 30 $g/m^2/h$. As the efficacy of the vehicle group was slightly better than that of the Chemin group, the microemulsion of Formulation A per se facilitated the recovery of skin barrier function so as to reduce abnormal transepidermal water loss.

Finally, both the Esperson group and the H.DXM group had a significant difference in comparison with the control group, which indicated that both groups can restore skin barrier functions and reduce abnormal transepidermal water loss. Besides, the H.DXM group had a low concentration of 0.05% DXM, which was only one fifth of that of 0.25% DXM in the Esperson group. However, the TEWL value of the Esperson group was about 20 $g/m^2/h$, and that of H.DXM group was about 15 $g/m^2/h$, which indicated the efficacy of the H.DXM group to restore skin barrier functions and reduce abnormal transepidermal water loss was better than that of the Esperson group, and such better efficacy indeed was unexpectedly excellent, so that the H.DXM group can be used to treat, ameliorate or ease the skin diseases like psoriasis as well.

(2) Skin Hydration Values Analysis

Figure 5B:
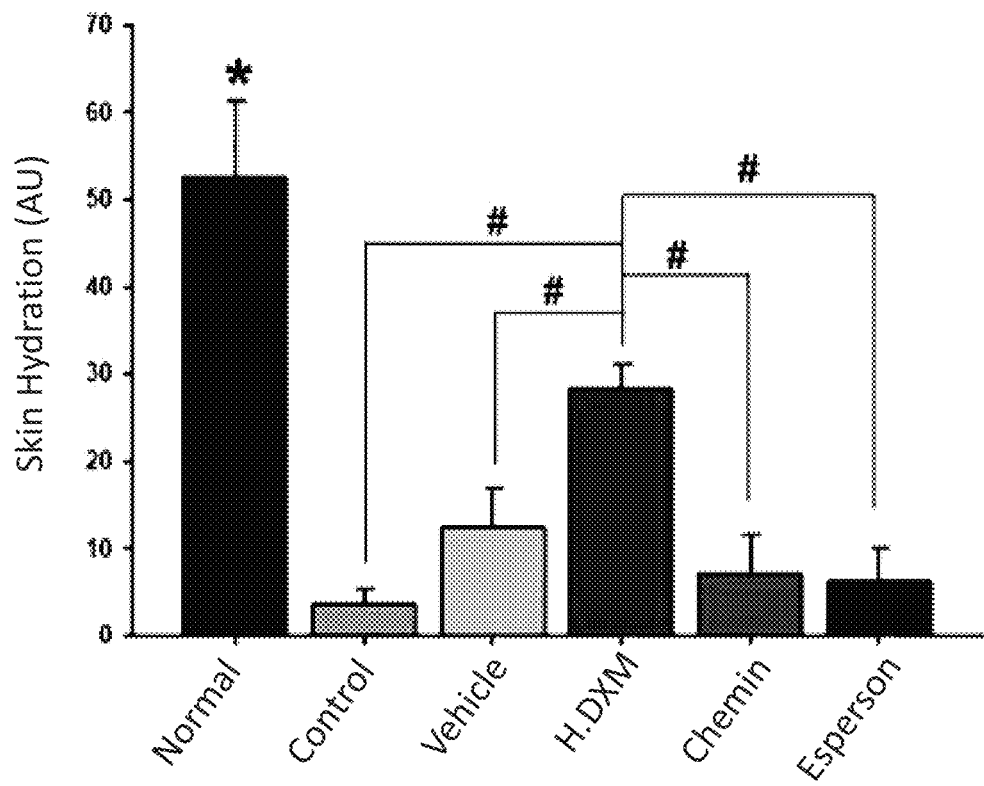

As shown in FIG. 5B, the normal group was not topically administered with IMQ, so the skin thereof was in a good condition and the skin hydration value was extremely high and higher than 50 AU, which had a significant difference in comparison with all the other groups. Besides, the H.DXM group had a second best skin hydration value, which was about 30 AU, and had a significant difference in comparison with those in both the Chemin group and the Esperson group. Although the H.DXM group had a concentration of 0.05% DXM, which was only one fifth of those of 0.25% DXM in both the Chemin group and the Esperson group, the efficacy of the H.DXM group to restore skin barrier functions and improve skin hydration was better than those of both the Chemin group and the Esperson group, so that the H.DXM group can be used to treat, ameliorate or ease the skin diseases like psoriasis as well. Finally, the vehicle group did not comprise DXM, and had a third best skin hydration value, which was better than those of both the Chemin group and the Esperson group, which indicated that the microemulsion of Formulation A per se facilitated the recovery of skin barrier function so as to improve skin hydration.

(3) Skin Erythema Values Analysis

Figure 5C:
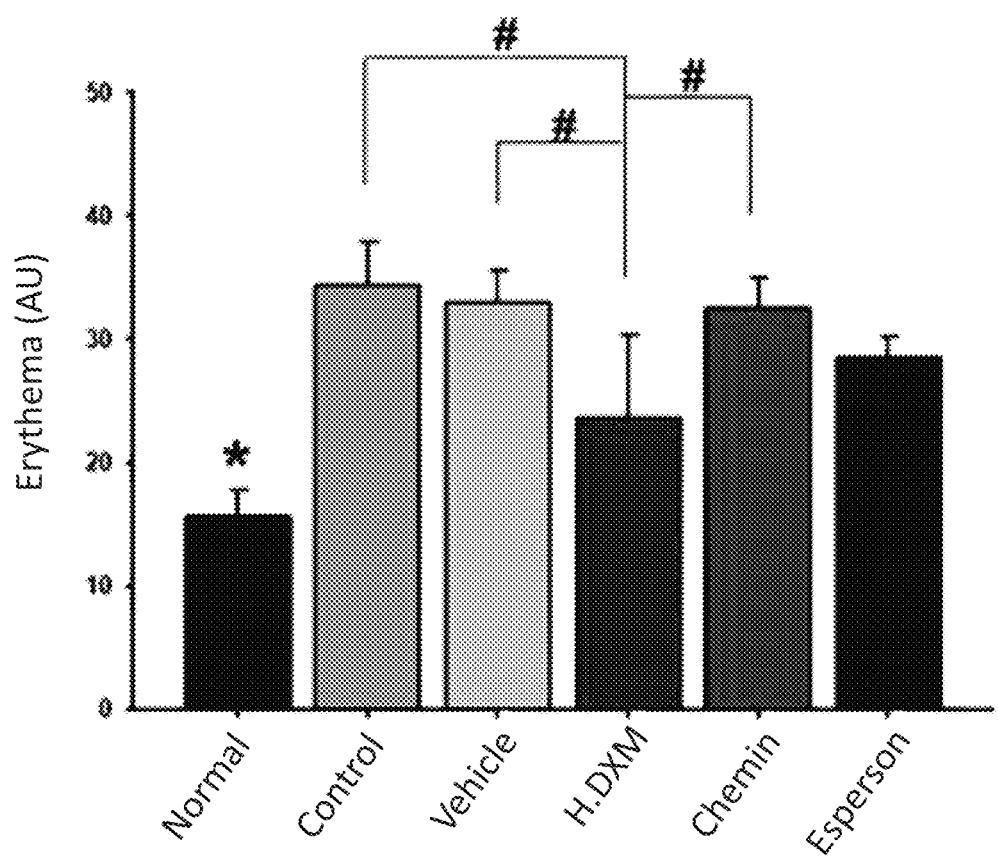

As shown in FIG. 5C, the normal group was not topically administered with IMQ, so the skin thereof was in a good condition and the skin erythema value was the lowest and lower than 20 AU, which had a significant difference in comparison with all the other groups. Besides, the H.DXM group had a second lowest skin erythema value, which was lower than 25 AU, and not only had a significant difference in comparison with those in both the Chemin group and the control group, but also was lower than that in the Esperson group. Although the H.DXM group had a concentration of 0.05% DXM, which was only one fifth of those of 0.25% DXM in both the Chemin group and the Esperson group, the efficacy of the H.DXM group to ameliorate skin erythema or skin inflammation was better than those of both the Chemin group and the Esperson group, so that the H.DXM group can be used to treat, ameliorate or ease the skin diseases like psoriasis as well.

Experiment 6: Histological Staining and the Expression Assessment Test of Proliferating Cell Nuclear Antigen (PCNA)

The groups in this experiment were the same as those in Experiment 5 and as shown in Table 4. The experimental animals and the experimental procedures were the same as Experiment 4, and the photos of mice dorsal side were shown in FIGS. 6A to 6F.

TABLE 4 the groups in the histological staining and the expression assessment test

Figure 6A:
FIGS. 6A to 6F are the mice dorsal photographs in Experiment 6.
Figure 6B:
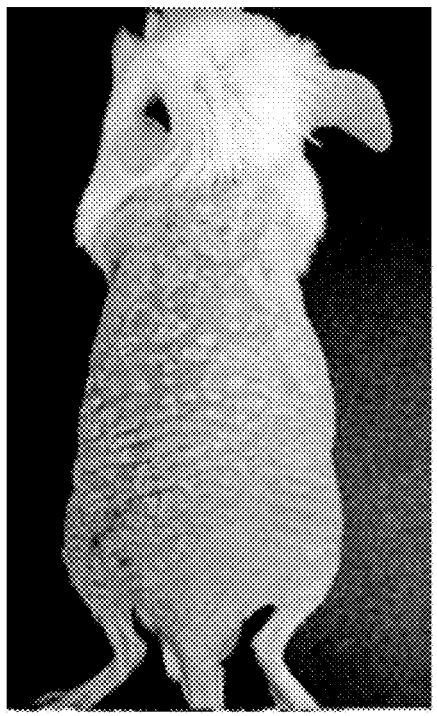
Figure 6C:
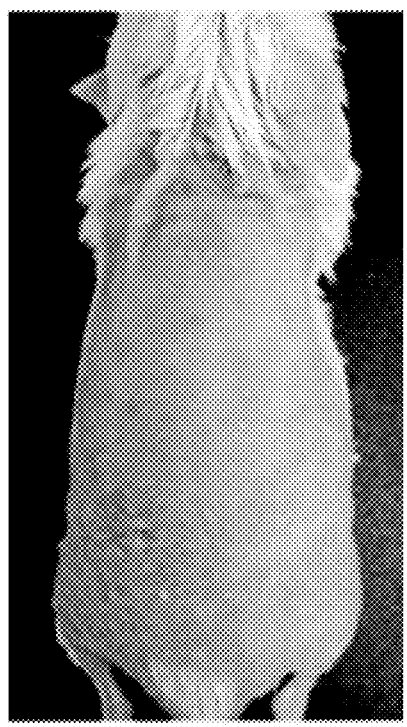
Figure 8A:
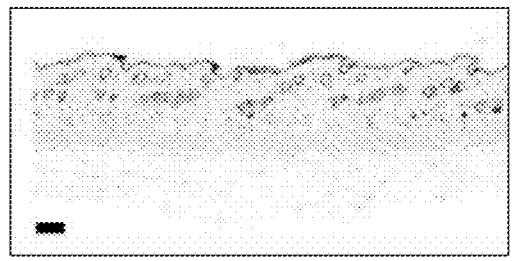
FIGS. 8A to 8F are immunohistochemical staining photographs for proliferating cell nuclear antigen (PCNA) of the histological sample sections of mice skin in Experiment 6.
Figure 8B:
Figure 8C:

| Group | Experimental procedures | Results |
|---|---|---|
| The normal group | No treatment | FIGS. 6A, 7A and 8A |
| The control group | a daily dose of 3.125 mg IMQ | FIGS. 6B, 7B and 8B |
| The vehicle group | a daily dose of 3.125 mg IMQ followed by a daily dose of 100 μL microemulsion of Formulation A | FIGS. 6C, 7C and 8C |

TABLE 4-continued the groups in the histological staining and the expression assessment test

Figure 6D:
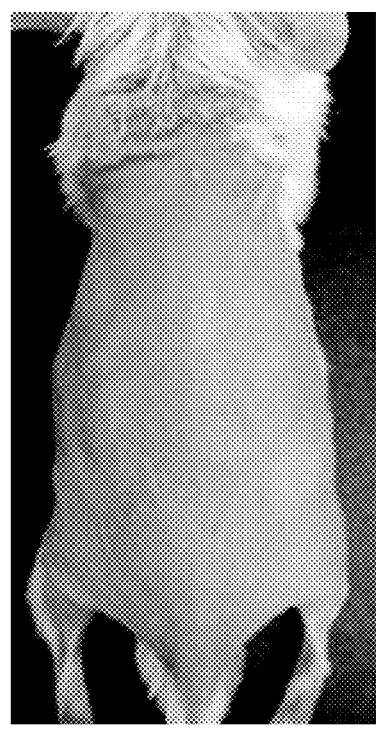
Figure 6E:
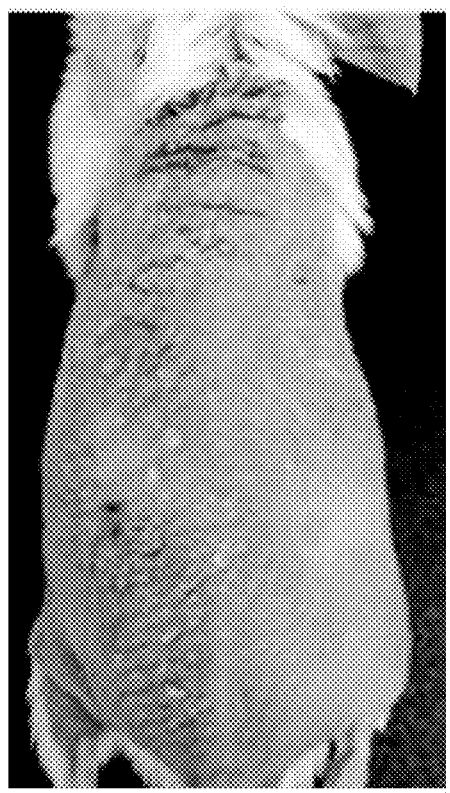
Figure 6F:
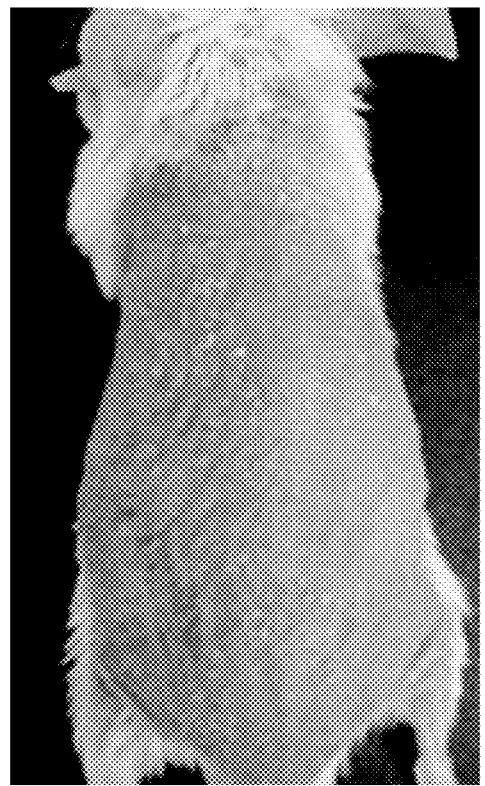
Figure 8D:
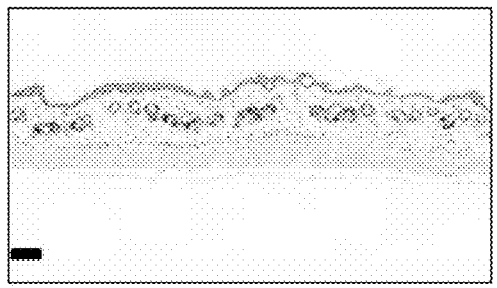
Figure 8E:
Figure 8F:

| Group | Experimental procedures | Results |
|---|---|---|
| The H.DXM group | a daily dose of 3.125 mg IMQ followed by a daily dose of 100 μL microemulsion mixture comprising the microemulsion of Formulation A and 0.05% Desoximetasone (DXM) | FIGS. 6D, 7D and 8D |
| The Chemin group | a daily dose of 3.125 mg IMQ followed by a daily dose of 60 mg Chemin oint (0.25% Desoximetasone ointment, Hua-***, Taiwan) | FIGS. 6E, 7E and 8E |
| The Esperson group | a daily dose of 3.125 mg IMQ followed by a daily dose of 60 mg Esperson ointment (0.25% DXM) | FIGS. 6F, 7F and 8F |

(1) The Mice Dorsal Appearance Observation

According to FIGS. 6A and 6D, the normal group had the best skin condition and had no conditions of dry skin, scales, epidermal acanthosis, parakeratosis, tortuous capillary dilatation in papillary dermis, erythema, and inflammatory cell infiltration. The H.DXM group had the second best skin condition. According to FIG. 6B, the control group had the worst skin condition and the conditions of dry skin, scales, epidermal acanthosis, parakeratosis, tortuous capillary dilatation in papillary dermis, erythema, and inflammatory cell infiltration were the worst. Finally, according to FIGS. 6C, 6E and 6F, the vehicle group had a skin condition better than those of both the Chemin group and the Esperson group, which indicated that the microemulsion of Formulation A even without DXM had the efficacy to ameliorate the conditions of dry skin, scales, epidermal acanthosis, parakeratosis, tortuous capillary dilatation in papillary dermis, erythema, and inflammatory cell infiltration. If the microemulsion of Formulation A was further mixed with DXM, the efficacy to ameliorate the conditions of dry skin, scales, epidermal acanthosis, parakeratosis, tortuous capillary dilatation in papillary dermis, erythema, and inflammatory cell infiltration was significantly improved so that the H.DXM group (the pharmaceutical microemulsion mixture of the present invention) can be used to treat, ameliorate or ease the skin diseases like psoriasis as well.

(2) Histological Staining of Mice Skin

The histochemical stain was carried as follows: The mice skin specimens were fixed in 10% formalin solution and embedded in paraffin after routine treatments. Sections of 5 μm thickness were cut and stained with hematoxylin and eosin, and examined under an optical microscope (Olympus BX41, Tokyo, Japan). The results were shown in FIGS. 7A to 7F, wherein the black line at the bottom in each figure was a scale bar representing 100 μm.

According to FIGS. 7A and 7D, the degree of epidermal thickening of the normal group was the lowest, and that of the H.DXM group was the second lowest and similar to that of the normal group. According to FIG. 7B, the control group had a high degree of epidermal thickening and desquamating issues, wherein the flake was shown in the upper part of the photograph. According to FIGS. 7C, 7E and 7F, the degree of epidermal thickening of the Esperson group was lower than those of both the vehicle group and the Chemin group, and such results accorded with those of the skin erythema values analysis shown in FIG. 5C.

Figure 9:
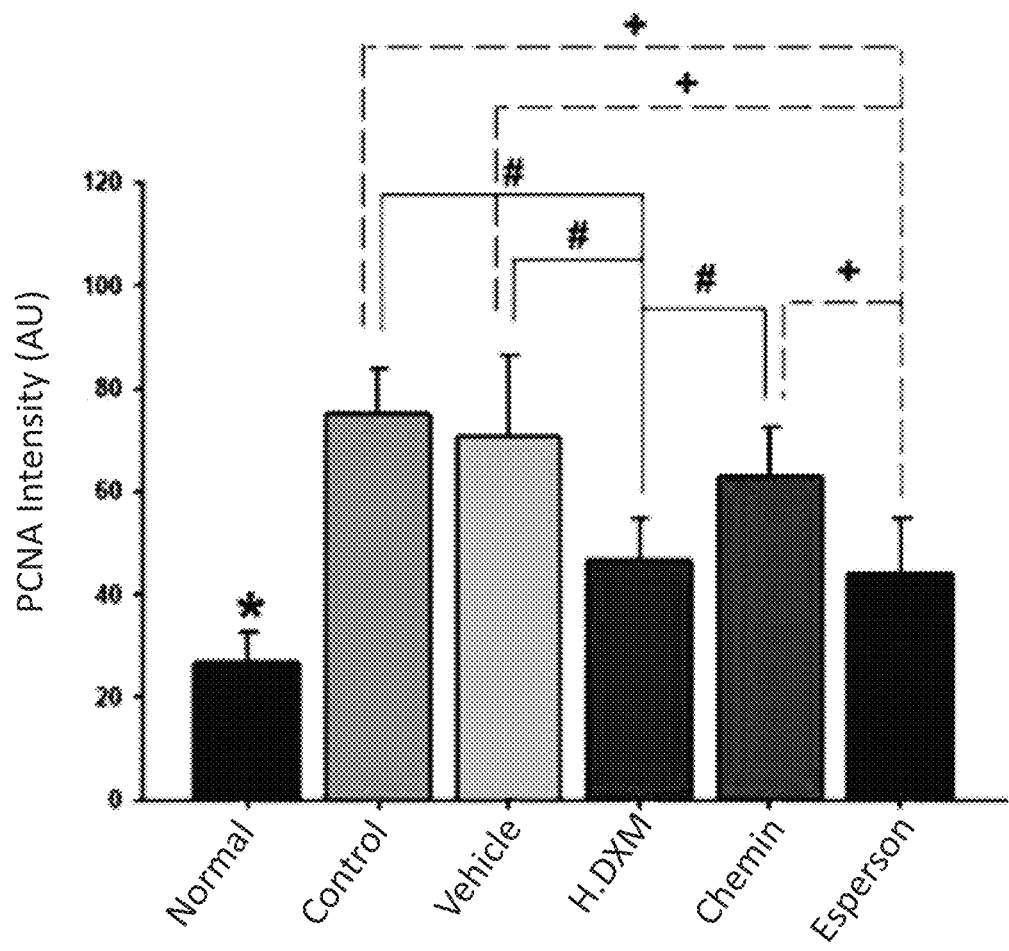
FIG. 9 is a diagram showing the comparison results of the expression assessment test of PCNA.

(3) The Immunohistochemical Staining for Proliferating Cell Nuclear Antigen (PCNA) of Mice Skin and the Immuno-Intensity Counting Thereof The steps in the immunohistochemical staining for PCNA and the immuno-intensity counting were the same as those in Experiment 4, except that the primary antibody against PCNA (purchased from Proteintech Group, Inc.) was adopted, wherein the groups along with the corresponding photographs of PCNA immunohistochemical staining were shown in FIGS. 8A to 8F, and the analysis result of PCNA expression intensity in each group was shown in FIG. 9, wherein * represented that the normal group was in comparison with all the other groups, and $P<0.05$; + represented that the Esperson group was in comparison with all the other groups, and $P<0.05$; and # represented that the H.DXM group was in comparison with all the other groups, and $P<0.05$.

According to FIGS. 8A to 8F, the result of the degree of epidermal thickening in each group was the same as those shown in FIGS. 7A to 7F.

According to FIG. 9, the normal group was not topically administered with IMQ, so the skin thereof was in a good condition and the PCNA expression intensity thereof was the lowest and lower than 30 AU, which had a significant difference in comparison with all the other groups. Second, the PCNA intensities of both the H.DXM group and the Esperson group were similar and were about 45 AU, which showed a significant difference in comparison with those of both the control group and the Chemin group. Although the H.DXM group had a concentration of 0.05% DXM, which was only one fifth of the 0.25% DXM in both the Chemin group and the Esperson group, the efficacy of the H.DXM group to inhibit the expression of proliferating cell nuclear antigen or abnormal epithelial cell proliferations was similar to or better than those of both the Chemin group and the Esperson group, so that the H.DXM group can be used to treat, ameliorate or ease the skin diseases like psoriasis as well.

Experiment 7: The Assessment Test for the Effective Concentration of DXM

There were 5 groups in this experiment as shown in Table 5, and the experimental animals and experimental procedures were the same as those in Experiment 4, wherein the mice dorsal photographs of each group on Day 6 were shown in FIGS. 10A to 10E.

TABLE 5

The groups in the assessment test for the effective concentration of DXM

Figure 10A:
FIGS. 10A to 10E are mice dorsal photographs in Experiment 7.
Figure 10B:
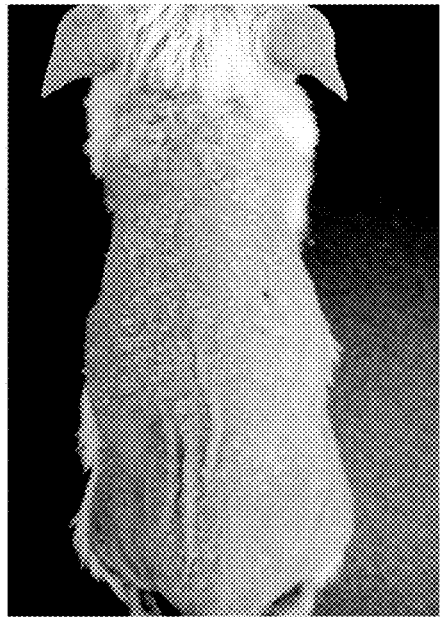
Figure 10C:
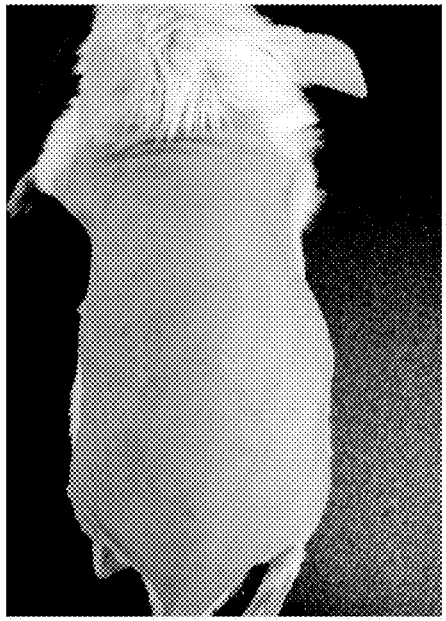
Figure 10D:
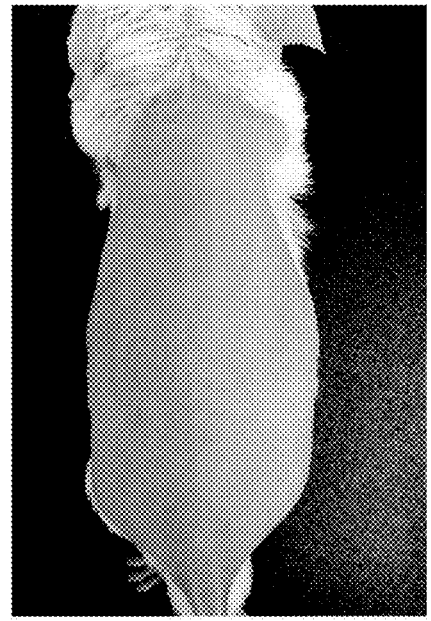
Figure 10E:
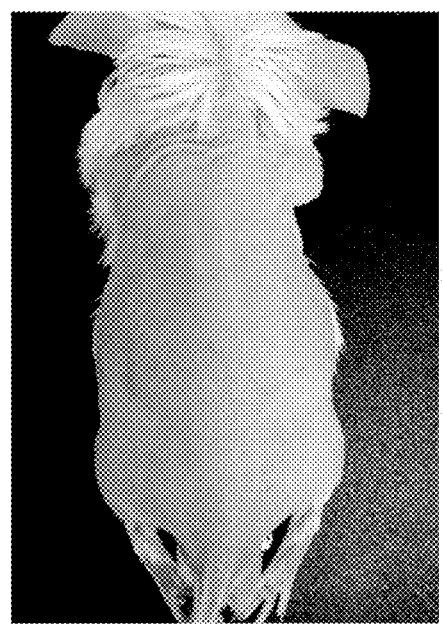
Figure 11A:
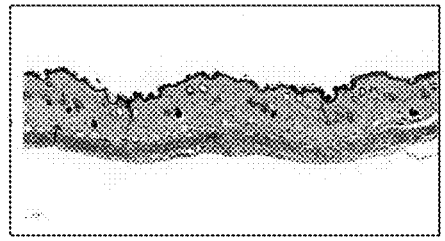
FIGS. 11A to 11E are the photographs of the histological sample sections of mice skin stained with hematoxylin and eosin in Experiment 7.
Figure 11B:
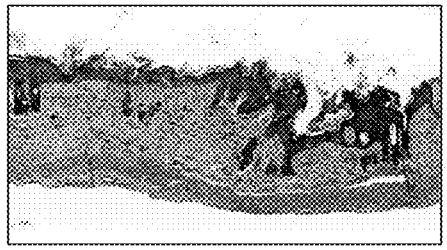
Figure 11C:
Figure 11D:
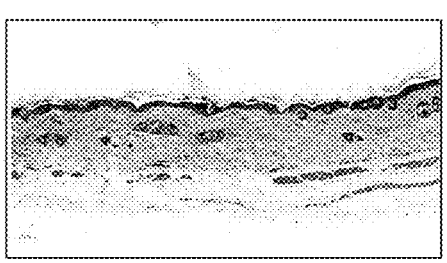
Figure 11E:
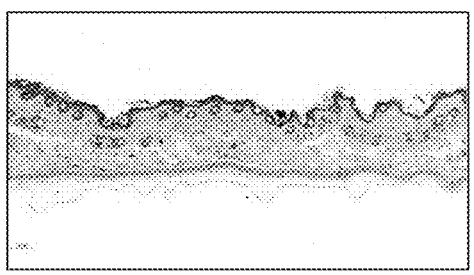

| Group | Experimental procedures | Results |
|---|---|---|
| The normal group | No treatment | FIGS. 10A and 11A |
| The control group | a daily dose of 3.125 mg IMQ | FIGS. 10B and 11B |
| The L.DXM group | a daily dose of 3.125 mg IMQ followed by a daily dose of 100 μL microemulsion mixture comprising the microemulsion of Formulation A and 0.01% Desoximetasone (DXM) | FIGS. 10C and 11C |
| The M.DXM group | a daily dose of 3.125 mg IMQ followed by a daily dose of 100 μL microemulsion mixture comprising the microemulsion of Formulation A and 0.025% Desoximetasone (DXM) | FIGS. 10D and 11D |
| The H.DXM group | a daily dose of 3.125 mg IMQ followed by a daily dose of 100 μL microemulsion mixture comprising the microemulsion of Formulation A and 0.05% Desoximetasone (DXM) | FIGS. 10E and 11E |

(1) The Observation for the Mice Dorsal Appearances

According to FIGS. 10A to 10E, all groups, except the control group, showed no conditions of dry skin, scales, epidermal acanthosis, parakeratosis, tortuous capillary dilatation in papillary dermis, erythema, and inflammatory cell infiltration. Therefore, the LDXM group, the microemulsion of Formulation A of the present invention mixed with 0.01% DXM, which was only the concentration of one twenty-fifth of that of the commercial medicament, still demonstrated the efficacy to significantly ameliorate the conditions of dry skin, scales, epidermal acanthosis, parakeratosis, tortuous capillary dilatation in papillary dermis, erythema, and inflammatory cell infiltration.

(2) Histological Staining of Mice Skin

The steps in the histological staining of mice skin were the same as those in Experiment 6(2), and the results were shown in FIGS. 11A to 11E; wherein the scale bar at the bottom in each figure represents 100 μm.

According to FIGS. 11A to 11E, the control group showed a severe condition of epidermal thickening, whereas all the other groups showed no condition of epidermal thickening. Therefore, the L.DXM group, the microemulsion of Formulation A of the present invention mixed with 0.01% DXM, which was only the concentration of one twenty-fifth of that of the commercial medicament, still demonstrated the efficacy to significantly ameliorate the conditions of skin inflammation and abnormal proliferations, so that the L.DXM group can be used to treat, ameliorate or ease the skin diseases like psoriasis as well.

(3) Transepidermal Water Loss Values Analysis for Mice Skin

Figure 12:
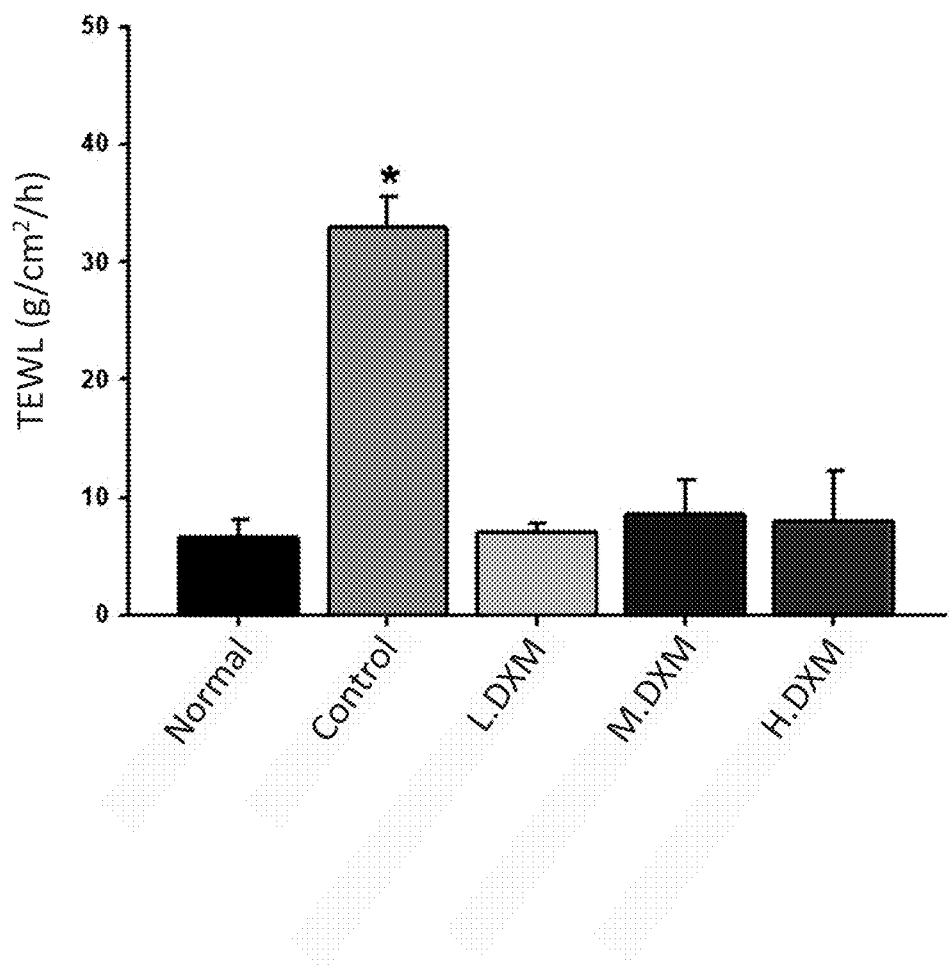
FIG. 12 is a diagram showing the comparison results of transepidermal water loss values in Experiment 7.

The steps in this experiment were the same as those in the (1) transepidermal water loss values analysis in Experiment 5, and the results were shown in FIG. 12, wherein * represented that the control group was in comparison with all the other groups, and P<0.05.

According to FIG. 12, the TEWL value of the control group was the highest and higher than 30 $g/m^2/h$; whereas those of the other groups were lower than 10 $g/m^2/h$. Therefore, the L.DXM group, the M.DXM group and the H.DXM group, the microemulsion of Formulation A of the present invention mixed with 0.01% DXM to 0.05% DXM, which were only the concentration of one twenty-fifth to one fifth of that of the commercial medicament, still demonstrated the efficacy to restore skin barrier functions and reduce abnormal transepidermal water loss, so that the L.DXM group, the M.DXM group and the H.DXM group can be used to treat, ameliorate or ease the skin diseases like psoriasis as well.

To sum up, the microemulsion of the present invention per se has the following advantages: (1) extremely low skin irritation potential; (2) good stability; (3) enhancing the skin penetration rate of the active ingredients and/or bioavailability thereof; (4) moisturizing skin or softening the stratum corneum of the skin; and (5) inhibiting the expression of P450 3A4. Therefore, the microemulsion of the present invention can serve as the vehicle of daily skin care products, thereby providing another safer and more effective option for consumers with problematic skin. Further, the microemulsion mixture of the present invention can be used by the subject having sensitive, injured or inflamed skin for daily skin care.

In addition to the aforementioned advantages, the microemulsion of the present invention is further mixed with desoximetasone to obtain a pharmaceutical microemulsion mixture, which has the following efficacies: (1) inhibiting abnormal epithelial cell proliferations; (2) treating, ameliorating or easing psoriasis or a skin symptom resulting from skin inflammation or autoimmunity; (3) lowering the required therapeutically effective concentration, whereas improving the therapeutic efficacy; (4) serving as a medicament for children or adolescents; and (5) improving or restoring skin barrier functions or skin hydration, reducing abnormal transepidermal water loss, or ameliorating erythema. In other words, the pharmaceutical microemulsion mixture of the present invention reduces the risk of side effects resulting from a long-term use of desoximetasone.

What is claimed is:

1. A pharmaceutical microemulsion mixture, comprising a microemulsion and an active ingredient, wherein the microemulsion comprises:
    a water phase composite, comprising a water solution and a moisturizer, wherein the water solution is an isotropic solution, and the moisturizer comprises sorbitol and glycerol, and based on the total amount of the isotropic solution, sorbitol and glycerol, the isotropic solution is in an amount from 31 weight percent to 39 weight percent, the sorbitol is in an amount from 45 weight percent to 55 weight percent, and the glycerol is in an amount from 12 weight percent to 18 weight percent;
    an oil phase composite, comprising silicone oil, squalene and triglyceride, and the weight ratio of the silicone oil, the squalene and the triglyceride is 8 to 12:0.8 to 1.2:2.5 to 3.5; and
    a surfactant composite, comprising polyoxyl hydrogenated castor oil, tween, polyethylene glycol (PEG) and propylene glycol (1,2-PG), and the weight ratio of the polyoxyl hydrogenated castor oil, the tween, the PEG and the 1,2-PG is 8 to 12:0.8 to 1.2:0.8 to 1.2:0.8 to 1.2; and
    based on a total amount of the water phase composite, the oil phase composite and the surfactant composite, the water phase composite is in an amount from 25 weight percent to 39 weight percent, the oil phase composite is in an amount from 8 weight percent to 22 weight percent, and the surfactant composite is in an amount from 53 weight percent to 67 weight percent; and
    the active ingredient is a substrate of cytochrome P450 3A4 enzyme, wherein the substrate of cytochrome P450 3A4 enzyme comprises a therapeutically effective concentration of desoximetasone, and the therapeutically effective concentration of desoximetasone is from 0.005 weight percent to 0.13 weight percent based on the total amount of the pharmaceutical microemulsion mixture.

2. The pharmaceutical microemulsion mixture as claimed in claim 1, wherein the moisturizer comprises sorbitol, and based on the total amount of the water phase composite, the sorbitol is in an amount of at least 40 weight percent;
    the oil phase composite comprises silicone oil, and based on the total amount of the oil phase composite, the silicone oil is in an amount of at least 60 weight percent; and
    the surfactant composite comprises polyoxyl hydrogenated castor oil, and based on the total amount of the surfactant composite, the polyoxyl hydrogenated castor oil is in an amount of at least 60 weight percent.

3. The pharmaceutical microemulsion mixture as claimed in claim 1, wherein the therapeutically effective concentration of desoximetasone is from 0.005 weight percent to 0.05 weight percent based on the total amount of the pharmaceutical microemulsion mixture.

4. A method for inhibiting the expression of proliferating cell nuclear antigen, comprising administering to a subject in need thereof an effective amount of the pharmaceutical microemulsion mixture as claimed in claim 1.

5. A method for inhibiting the expression of proliferating cell nuclear antigen, comprising administering to a subject in need thereof an effective amount of the pharmaceutical microemulsion mixture as claimed in claim 2.

6. A method for inhibiting the expression of proliferating cell nuclear antigen, comprising administering to a subject in need thereof an effective amount of the pharmaceutical microemulsion mixture as claimed in claim 3.

7. A method for treating, ameliorating or easing a skin symptom resulting from skin inflammation, comprising administering to a subject in need thereof an effective amount of the pharmaceutical microemulsion mixture as claimed in claim 1.

8. A method for treating, ameliorating or easing a skin symptom resulting from skin inflammation, comprising administering to a subject in need thereof an effective amount of the pharmaceutical microemulsion mixture as claimed in claim 2.

9. A method for treating, ameliorating or easing a skin symptom resulting from skin inflammation, comprising administering to a subject in need thereof an effective amount of the pharmaceutical microemulsion mixture as claimed in claim 3.

10. A method for treating, ameliorating or easing a skin symptom resulting from autoimmunity, comprising administering to a subject in need thereof an effective amount of the pharmaceutical microemulsion mixture as claimed in claim 1.

11. A method for treating, ameliorating or easing psoriasis, comprising administering to a subject in need thereof an effective amount of the pharmaceutical microemulsion mixture as claimed in claim 1.

12. A method for treating, ameliorating or easing psoriasis, comprising administering to a subject in need thereof an effective amount of the pharmaceutical microemulsion mixture as claimed in claim 2.

13. A method for treating, ameliorating or easing psoriasis, comprising administering to a subject in need thereof an effective amount of the pharmaceutical microemulsion mixture as claimed in claim 3.

14. A method for improving or restoring skin barrier functions or skin hydration, reducing abnormal transepidermal water loss, or ameliorating erythema or abnormal epithelial cell proliferations, comprising administering to a subject in need thereof an effective amount of the pharmaceutical microemulsion mixture as claimed in claim 1, wherein the subject has an injured skin or skin inflammation.

15. A medicament for children or adolescents, comprising an effective amount of the pharmaceutical microemulsion mixture as claimed in claim 1.

16. A method for improving the efficacy of skin care, comprising administering to a subject in need thereof an effective amount of the pharmaceutical microemulsion mixture as claimed in claim 1.

17. A method for preventing, treating or ameliorating skin cancer, comprising administering to a subject in need thereof an effective amount of the microemulsion mixture, wherein the microemulsion mixture comprises a microemulsion and an active ingredient, wherein the microemulsion comprises:
   a water phase composite, comprising a water solution and a moisturizer, wherein the water solution is an isotropic solution, and the moisturizer comprises sorbitol and glycerol, and based on the total amount of the isotropic solution, sorbitol and glycerol, the isotropic solution is in an amount from 31 weight percent to 39 weight percent, the sorbitol is in an amount from 45 weight percent to 55 weight percent, and the glycerol is in an amount from 12 weight percent to 18 weight percent;
   an oil phase composite, comprising silicone oil, squalene and triglyceride, and the weight ratio of the silicone oil, the squalene and the triglyceride is 8 to 12:0.8 to 1.2:2.5 to 3.5; and
   a surfactant composite, comprising polyoxyl hydrogenated castor oil, tween, polyethylene glycol (PEG) and propylene glycol (1,2-PG), and the weight ratio of the polyoxyl hydrogenated castor oil, the tween, the PEG and the 1,2-PG is 8 to 12:0.8 to 1.2:0.8 to 1.2:0.8 to 1.2; and
   based on a total amount of the water phase composite, the oil phase composite and the surfactant composite, the water phase composite is in an amount from 25 weight percent to 39 weight percent, the oil phase composite is in an amount from 8 weight percent to 22 weight percent, and the surfactant composite is in an amount from 53 weight percent to 67 weight percent; and
   the active ingredient is a substrate of cytochrome P450 3A4 enzyme.

18. A method for preventing, treating or ameliorating inflammation, comprising administering to a subject in need thereof an effective amount of the microemulsion mixture, wherein the microemulsion mixture comprises a microemulsion and an active ingredient, wherein the microemulsion comprises:
   a water phase composite, comprising a water solution and a moisturizer, wherein the water solution is an isotropic solution, and the moisturizer comprises sorbitol and glycerol, and based on the total amount of the isotropic solution, sorbitol and glycerol, the isotropic solution is in an amount from 31 weight percent to 39 weight percent, the sorbitol is in an amount from 45 weight percent to 55 weight percent, and the glycerol is in an amount from 12 weight percent to 18 weight percent;
   an oil phase composite, comprising silicone oil, squalene and triglyceride, and the weight ratio of the silicone oil, the squalene and the triglyceride is 8 to 12:0.8 to 1.2:2.5 to 3.5; and
   a surfactant composite, comprising polyoxyl hydrogenated castor oil, tween, polyethylene glycol (PEG) and propylene glycol (1,2-PG), and the weight ratio of the polyoxyl hydrogenated castor oil, the tween, the PEG and the 1,2-PG is 8 to 12:0.8 to 1.2:0.8 to 1.2:0.8 to 1.2; and
   based on a total amount of the water phase composite, the oil phase composite and the surfactant composite, the water phase composite is in an amount from 25 weight percent to 39 weight percent, the oil phase composite is in an amount from 8 weight percent to 22 weight percent, and the surfactant composite is in an amount from 53 weight percent to 67 weight percent; and
   the active ingredient is a substrate of cytochrome P450 3A4 enzyme.

19. An antibacterial or antifungal method, comprising administering to a subject in need thereof an effective amount of the microemulsion mixture, wherein the microemulsion mixture comprises a microemulsion and an active ingredient, wherein the microemulsion comprises:
   a water phase composite, comprising a water solution and a moisturizer, wherein the water solution is an isotropic solution, and the moisturizer comprises sorbitol and glycerol, and based on the total amount of the isotropic solution, sorbitol and glycerol, the isotropic solution is in an amount from 31 weight percent to 39 weight percent, the sorbitol is in an amount from 45 weight percent to 55 weight percent, and the glycerol is in an amount from 12 weight percent to 18 weight percent;

an oil phase composite, comprising silicone oil, squalene and triglyceride, and the weight ratio of the silicone oil, the squalene and the triglyceride is 8 to 12:0.8 to 1.2:2.5 to 3.5; and a surfactant composite, comprising polyoxyl hydrogenated castor oil, tween, polyethylene glycol (PEG) and propylene glycol (1,2-PG), and the weight ratio of the polyoxyl hydrogenated castor oil, the tween, the PEG and the 1,2-PG is 8 to 12:0.8 to 1.2:0.8 to 1.2:0.8 to 1.2; and based on a total amount of the water phase composite, the oil phase composite and the surfactant composite, the water phase composite is in an amount from 25 weight percent to 39 weight percent, the oil phase composite is in an amount from 8 weight percent to 22 weight percent, and the surfactant composite is in an amount from 53 weight percent to 67 weight percent; and the active ingredient is a substrate of cytochrome P450 3A4 enzyme.

\* \* \* \* \*